US006458588B1

(12) United States Patent
Arnaout et al.

(10) Patent No.: US 6,458,588 B1
(45) Date of Patent: Oct. 1, 2002

(54) RENAL STEM CELLS AND USES THEREOF

(75) Inventors: M. Amin Arnaout, Chestnut Hill; Peter G. Linde, Dedham, both of MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/826,698

(22) Filed: Apr. 5, 2001

Related U.S. Application Data

(60) Provisional application No. 60/265,552, filed on Jan. 31, 2001.

(51) Int. Cl.$^7$ .................................................. C12N 5/08
(52) U.S. Cl. ...................................... 435/369; 435/7.21
(58) Field of Search .............................. 435/7.21, 369; 424/93.21, 93.7

(56) References Cited

U.S. PATENT DOCUMENTS

| | | |
|---|---|---|
| 6,060,270 A | 5/2000 | Humes |
| 6,149,902 A | 11/2000 | Artavanis-Tsakonas et al. |
| 6,150,164 A | 11/2000 | Humes |

OTHER PUBLICATIONS

Abrahamson et al., "Origins and formation of microvasculature in the developing kidney", *Kidney International*, 54:S–7S–11, (1998).

Clarke et al., "Generalized Potential of Adult Neural Stem Cells", *Science*, 288:1660–1663, (2000).

Gussoni et al., "Dystrophin expression in the mdx mouse restored by stem cell transplantation", *Nature*, 401:390–394, (1999).

Kanellis et al., "Vascular endothelial growth factor is a survival factor for renal tubular epithelial cells", *The American Journal of Physiological Renal Physiol.*, 278:F905–F915, (2000).

Robert et al., "Coexpression of neuropilin–1, Flk1, and $VEGF_{164}$ in developing and mature mouse kidney glomeruli", *The American Journal of Physiological Renal Physiol.*, 279:F275–F282, (2000).

Sakurai et al., "In vitro branching tubulogenesis: Implications for developmental and cystic disorders, nephron number, renal repair, and nephron engineering", *Kidney International*, 54:14–26, (1998).

Slack, "Stem Cells in Epithelial Tissues", *Science*, 287:1431–1433, (2000).

*Primary Examiner*—James Ketter
(74) *Attorney, Agent, or Firm*—Fish & Richardson, P.C.

(57) ABSTRACT

Flk-1 positive/Sca-1 negative renal stems cells and uses thereof are described. The cells are useful for the regeneration of damaged kidney tissue, the generation of artificial kidneys and the delivery of transgenes.

14 Claims, No Drawings

RENAL STEM CELLS AND USES THEREOF

RELATED APPLICATION INFORMATION

This application claims priority from provisional application Ser. No. 60/265,552, filed Jan. 31, 2001.

TECHNICAL FIELD

This invention relates to stem cell, and more particularly to renal stem cells isolated from kidney tissue.

BACKGROUND

Renal failure, whether arising from an acute or chronic decline in renal function, is a grave condition that can result in substantial or complete failure of the filtration, reabsorption, endocrine, and homeostatic functions of the kidney. It would be highly desirable to obtain cells, e.g., stem cells, capable of developing into cells that could supply some or all of the functions provided by the kidney. Such cells might be capable of producing functional renal cells or regenerating a functioning kidney, in whole or in part. The functional renal cells or regenerated kidney could be implanted into the donor of the stem cells as an autologous transplant or into another patient. Such renal stem cells could be used to construct an artificial kidney from biological and non-biological components. An artificial kidney might be implanted or used ex vivo to replace or supplement renal function.

Stem cells have been identified in adult mouse brain (Clarke et al. 2000 *Science* 288:1660) and from 3–5 week old mouse skeletal muscle (Gussoni et al. 1999 *Nature* 401:390). It has also been suggested that most, if not all epithelial tissues, including the kidney, contain stem cells (Slack 2000 *Science* 287:1431). Indeed, it has been suggested that the nephron may be an "epithelial structural-proliferative" unit, analogous to a liver lobule, an acinus of salivary gland, a stomach gland, or an intestinal crypt (Slack 2000 *Science* 287:1431).

SUMMARY

The invention features renal stem cells isolated from kidney tissue, including adult kidney. The stem cells are capable of contributing to the formation of metanephric tubule cells in fetal or adult kidney.

The invention features a composition comprising isolated renal cells that express Flk-1 and do not substantially express Sca-1. The composition can contain a population of cells that express cell surface Flk-1 wherein less than 30%, less than 20%, less than 10%, less than 5%, less than 1%, less than 0.5%, less than 0.1%, less than 0.01% express cell surface Sca-1. Preferably at least 50%, at least 60%, at least 70%, at least 80%, at least 90%, at least 95%, at least 99% of the cells in the composition express Flk-1 and do not substantially express Sca-1. Preferably at least 50%, at least 60%, at least 70%, at least 80%, at least 90%, at least 95%, at least 99% of the cells in the composition are renal cells. In various embodiments the cells are human cells, the cells contain a transgene, the cells contain a transgene that encodes a therapeutic protein.

The invention also feature a method for isolating renal stem cells, comprising: obtaining isolated kidney cells; and purifying from the isolated kidney cells a population of cells that express Flk-1 and do not substantially express Sca-1. In certain embodiments the isolation step comprising contacting kidney cells with an antibody the selectively binds to Flk-1.

The invention also feature a method for treating kidney damage in a patient, the method comprising injecting into a damaged kidney of the patient a therapeutically effective amount of renal stem cells that express Flk-1 and do not substantially express Sca-1. In certain embodiments the renal stem cells are derived from the patient or a matched donor.

The details of one or more embodiments of the invention are set forth in the accompanying drawings and the description below. Other features, objects, and advantages of the invention will be apparent from the description and drawings, and from the claims.

DETAILED DESCRIPTION

Isolation of Stem Cells from Adult Kidney

In an effort to isolate kidney progenitor cells from adult mammalian kidney, various progenitor cell markers were employed. For example, Flk-1 (Fetal Liver Kinase-1 or VEGF-R2) is found on angioblasts in metanephroi and is a receptor for vascular endothelial growth factor (VEGF). It has been shown to be present in subpopulation of embryonic stem cells that serve as vascular progenitors (Yamashita et al. 2000 *Nature* 408:92). Flk-1 has been suggested to be critical for embryonic vasculogenesis, large vessel tube formation and hematopoesis, as demonstrated by knock-out mice (Shalaby et al. 1995 *Nature* 376:62). Moreover, VEGF has been shown to induce proliferation of tubular epithelial cells, and tubular epithelia cells in metanephroi have been shown to be positive for Fkl-1 and Flt-1 (VEGF-R1) (Kanellis et al. 2000 *Am. J. Renal Physiol.* 278:F905; Tufro et al. 1999 *J. Am. Soc. Nephrol.* 10:2125). Sca-1 is an important marker of stem cells isolated from adult muscle (Gussoni et al. 1999 *Nature* 401:390). Thus, Flk-1 and Sca-1 were investigated as markers for renal stem cells.

FACS analysis of kidney cells revealed that 65% of the kidney side population (SP) cells (as determined by Hoechst 33342 dye exclusion) stain positively for Sca-1. When sorted by FACS, the Sca-$1^+$cells have been initially characterized as being cytokeratin negative and vimentin positive, excluding the possibility that these cells are epithelial cells. When whole kidney sections were stained for Sca-1 expression, many cells in the DCT, CD, TAL scored positive. Thus, there are Sca-$1^+$cells that comprise less than 1% of the total cells isolated from whole adult kidney and which are only present in epithelial structures, yet are cytokeratin negative. The properties of these cells are consistent with the proposed role for residual stem cells in epithelial-proliferative units. In view of these results an earlier work on isolation of stem cells from various sources, it was expected that the desired renal stem cells would be Sca-$1^+$.

Renal stem cells were isolated from adult mouse kidney using the following procedure. Six kidneys were extracted from C57BL/6-Rosa 26 (Jackson Laboratories) mice after phenobarbital anesthesia and total body perfusion with DMEM/F12 (GIBCO/BRL) media while the heart was still beating. The collagenous sheaths surrounding the kidneys were removed by dissection. The kidneys were then minced into 2 mm diameter pieces using a fine scalpel. The pieces were placed into DMEM/F12 media containing 5 mg/ml of Collagenase Type 2 (Worthington), with 1 mM $CaCl_2$, incubated with gentle stirring for 1 hour at 37° C. in a water bath. The cells were collected by centrifugation and resuspended in DMEM/F12 with 2% fetal calf serum (FCS) by gentle swirling. The cells were allowed to stand on ice for 10 min and were then filtered through 70 micron mesh filter (Fisher). The cells were counted and suspended in DMEM/F12/2% FCS at a concentration of 1 million cells/ml.

To stain for Flk-1 and Sca-1, 30 µl Flk-1-PE linked antibody (BD PharMingen; San Diego, Calif.) and 30 µl Sca-1-FITC linked antibody (BD PharMingen) were added to about 15 million cells. The cells were incubated with the antibodies for one hour at 37° C. Appropriate negative cell controls for FITC and PE staining were prepared. The cells were sorted by FACS (y-axis: Flk-PE and x-axis: Sca-FITC). Flk-1 positive/Sca-1 negative cells in the Flk-1/Sca-1 profile were identified by comparison to Flk-1 negative controls and collected. This process yielded approximately 9% Flk-1 positive cells per total sorted cells.

As an alternative to the above procedure for marking Sca-1 and Flk-1, biotin-coupled primary Flk-1 antibodies and primary Sca-1 antibodies (BD PharMingen or Caltag) can be used. In general, and method for preparing Flk-1 positive/Sca-1 negative cells can be used.

Stem Cells Isolated from Adult Kidney Contribute to the Formation of Metanephric Tubule Cells in Adult Kidney The Fkl-1 postive/Sca-1 negative stem cells isolated as described above were injected into adult mice and were found to contribute to the formation of metanephric tubule cells in adult kidney. Briefly, stem cells isolated from C57BL/6-Rosa 26 mice (Jackson Laboratories) were collected by centrifugation at 2000 rpm in table top centrifuge and were resuspended in Stem Cell Media (DMEM (Sigma), 20 mM Hepes, 5% FBS (Qualified, GIBCO), 0.1 mM mercaptoethanol, 1:100 PCN/Strep 5000/5000 formulation (GIBCO), 0.1 M non-essential amino acids) at a concentration of 100 cells/µl. The cells were drawn into a 1 cc tuberculin syringe that was then stored on ice. A C57Bl/6 mouse was prepped and anesthetized with phenobarbital. The right kidney was surgically exposed via sharp and blunt dissection, and 20 µl of prepared stem cells (2000 cells) were injected at multiple sites into the kidney at 2–4 mm depth. The incision sites were surgically closed and the mouse was allowed to recover for 8 days. The mouse was then sacrificed and its circulation was flushed with PBS followed by PBS with 30% sucrose. The kidneys were removed intact and incubated in PBS/30% sucrose for 1 hour at 4° C. To look for transplanted cells, the kidneys were embedded in OTC, frozen and sectioned into 10 micron slices and placed on slides. The tissue slices were fixed in 2% paraformaldehyde/PBS for 2 min at room temperature.

Alternatively, the slices can be fixed in 0.5% glutaraldehyde at room temperature for 1 hour. The slides were briefly washed with PBS, treated with X-gal reagent (4.175 ml 100 mM Na Phosphate buffer (pH 7.3), 10 µl 500 mM $MgCl_2$, 40 µl 1M KCl, 300 µl of K4 solution (1.056 gm $K_4[Fe(CN)_6]$ in 50 ml), 300 µl of $K_3$ solution (0.823 g $K_3[Fe(CN)_6]$ in 50 ml), 125 µl 2% X-gal powder/Dimethyl formamide solution), and incubated overnight at 37° C.

When the stained tissue samples were examined, lacZ expressing cells, i.e., cells that were derived from the donor Rosa 25 (blue) mice, were found to be incorporated into metanepheric tubule cells, indicating that the transplanted stem cells can contribute to the formation of differentiated kidney tissue in adult mice. Thus, surprisingly, cells having stem cells properties were Flk-1 positive/Sca-1 negative, contrary to current expectations based on the literature.

The Role of Isolated Flk-1 Postive Sca-1 Negative Stem Cells in Renal Development The role of isolated Flk-1 postive/Sca-1 negative stem cells in renal development can be tested as follows.

Kidneys from C57BL/6-Rosa 26 (Jackson Laboratories) mice are extracted after total body perfusion with DMEM/F12 (GIBCO) media while heart is still beating. The collagneous sheath is removed by dissection. Minced kidneys are treated with DMEM/F 12media containing collagenase for 1 hour at 37° C. Centrifuged cells are filtered and then resuspended at a concentration of 30 million cells/ml. The cells are then double stained with Flk-1 and Sca-1 antibodies and sorted by FACS analysis. Flk-1 positive/Sca-1 Negative cells are collected and concentrated to 105 cells/ml.

For juvenile adult in vivo injection, a wild-type C57BL/6 mouse is prepped and anesthetized. One kidney is surgically exposed, and cells are injected at multiple sites in the kidney. The mice are allowed to recover 8 days before being sacrificed. The kidney is harvested, fixed, frozen sectioned and finally developed with x-gal reagent to detect transplanted cells.

For in vitro cell injection into day 13 metanephroi using microinjection technique, an apparatus and injection similar to that described by Joyner (Joyner, *Gene Targeting: A Practical Approach*, New York, Oxford University Press, 288, 2000) is used. The resultant organ cultures are then grown over a spinal cord inducer using a standard transfilter system (Grobstein 1956 *Exp. Cell Res.* 10:424–40,1956).

Collected cells and incorporated injected cells are analyzed using standard immunohistochemical techniques. For example, FACS sorted cells are stained for Vimentin (Fibrobast/non-epithelial marker), Cytokeratin 8/18 (epithelial marker), GP330 (proximal tubule), TamHorsfall protein (distal tubule/thick ascending limb), Dolichos Biflorus Agglutinin (collecting tubule). The last three markers are surface markers, and they can be detected without permeabilization with detergent. Vimentin and Cytokeratin are intracellular markers and require permeabilization for detection. Briefly, the cells are fixed onto a microscope coverslip and then permeabilized where appropriate. The sample are exposed to primary antibodies, washed and then exposed to a secondary antibody linked with an appropriate detectable marker, e.g., FITC or CY-3. The cells are reserved and examined by fluorescent microscopy. Similar protocols are employed to investigate the presence of differentiation markers in fixed metanephroi or juvenile kidneys that have been injected with stem cells. It is expected that as the injected stem cells incorporate into differentiated nephron structures, their surface markers will change to reflect those of the structures into which they have become incorporated.

In addition, the developmental potential of the stem cells can be investigated by injection into other organs (liver, muscle, heart, and bone marrow) to test their multipotency. Clarke et al. describes protocols for investigating the development potential of stem cells (Clarke et al. 2000 Science 288:1660).

Renal Stem Cells and Repair of Ischemic Injury

In order to investigate the possibility that renal stem cells can play a role in repair of damaged kidney tissue, renal stem cells are injected in vivo into a kidney that is in the post-ischemic recovery phase. Briefly, the renal pedicle of an anesthetized mouse is clamped for 30 minutes to induce kidney ischemia. Renal stem cells are then injected into the juxta-medullary region (approximately 2000 cells at a depth of 2–4 mm). After 2 weeks of recovery, immunohistochemical analysis is used as described above to look for differentiated 30 cells surface markers GP330, Tamm-Horfall, Dolichos Biflorous, and the like. Post-incorporation differentiation status can then be compared to pre-injection marker status.

Use of Renal Stem Cells

The renal stem cells of the invention can be used to supplement or substitute for kidney cells that have been destroyed or have reduced function. Thus, they can be used to treat patients having poor or no kidney function. The renal stem cells of the invention or cells derived from the renal stem cells of the invention may be capable of performing the filtration and reabsorptive/secretive functions of the kidney.

Because the cells can be transfected with a DNA molecule of interest, they can be used to introduce a gene and the capacity to produce the protein encoded by the gene into a patient. Thus, the renal stem cells of the invention can also be used for gene therapy.

The renal stem cells or cells derived from the renal stem cells can be introduced into a patient surgically or by infusion. The introduced cells can harbor a transgene, i.e., a gene that was introduced into the cells or the cells from which they were derived by genetic engineering. Renal stem cells bearing a transgene can be used to treat a number of kidney disorders. For example, genes encoding erythropoeitin or insulin can be introduced into a kidney stem cell. For treatment of anemia associated with renal failure or diabetes it can be useful to introduce into a patient a stem cells modified to express erythropoeitin or insulin.

The renal stem cells can be stably or transiently transfected with DNA encoding any therapeutically useful polypeptide.

The renal stem cells of the invention can also be provided with a transgene encoding VEGF or some other factor that can promote growth and or differentiation of cells.

A transgene is usually introduced into a cell in the form of a vector, i.e., a nucleic acid molecule capable of transporting another nucleic acid to which it has been linked. The vector can be a viral vector (e.g., replication defective retroviruses, adenoviruses and adeno-associated viruses), wherein additional DNA segments can be ligated into the viral genome. Certain vectors are capable of autonomous replication in a host cell into which they are introduced. Other vectors (e.g., non-episomal mammalian vectors) are integrated into the genome of a host cell upon introduction into the host cell, and thereby are replicated along with the host genome. Expression vectors are capable of directing the expression of genes to which they are operably linked.

The recombinant expression vectors that can be introduced into renal stem cells include one or more regulatory sequences that are operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the cell in which the transgene is to be expressed, the level of expression of protein desired, etc.

Another aspect of the invention pertains to host cells into which a recombinant expression vector of the invention has been introduced. The terms "host cell" and "recombinant host cell" are used interchangeably herein. It is understood that such terms refer to the particular subject cell and to the progeny or potential progeny of such a cell. Because certain modifications may occur in succeeding generations due to either mutation or environmental influences, such progeny may not, in fact, be identical to the parent cell, but are still included within the scope of the term as used herein.

Vector DNA can be introduced into cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride coprecipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those that confer resistance to drugs, such as G418, hygromycin and methotrexate. Nucleic acid encoding a selectable marker can be introduced into a host cell on the same vector as that encoding the transgene or can be introduced on a separate vector. Cells stably transfected with the introduced nucleic acid can be identified by drug selection (e.g., cells that have incorporated the selectable marker gene will survive, while the other cells die).

The transfected cells can be introduced into a patient by injection into the kidney or into the bloodstream.

The stem cells of the invention or cells derived from the stem cells of the invention (e.g., epithelial cells endothelial cells, mesangial cells, vascular smooth muscle cells, and pericytes) can be used to construct artificial kidney systems. Such a system can be based on a hollow fiber filtration system.

In one example of a filtration device, the stem cells of the invention or differentiated progeny thereof are grown on the interior of hollow fibers having relatively high hydraulic conductivity (i.e., ultrafiltration coefficient). The hollow fiber passes through a chamber that is provided with a filtrate outlet port. Arterial blood containing metabolic wasteland other unwanted material is introduced into one end of the hollow fiber through an inlet port. Blood passed through the fiber and exits the other end of the fiber through an outlet port where it passed into the patient's vascular venous flow. As blood passes through the fiber, filtrate pass through the cells lining the interior of the fiber and through the hollow fiber itself. This filtrate then passes out of the chamber containing the fiber through the filtrate outlet port. The device preferably includes many such hollow fibers each of which can be in its own chamber. Alternatively many, many hollow fibers (100–100,000 or even more) can be bundled together in a single chamber.

The cells of the invention can be used to create a tubule-processing device. In such a device the stem cells of the invention or differentiated cells derived from the stem cells of the invention can be grown in a layer on the exterior of the semipermeable hollow fiber. The fiber is placed in a chamber that is provided with an inlet port and an outlet port. As ultrafiltrate from filtered blood flows through the chamber, reabsorbant passes through the cell layer and through the wall of the fiber into the lumen of the fiber from which it can be directed back into the patient's systemic circulation. Ultrafiltrate that is not reabsorbed passes through the outlet port of the chamber.

In the devices described above, it can be desirable to coat the fiber surface that will bear the cell layer with extracellular matrix components. For example, the fiber can be coated with materials such as collagen (e.g., Type I collagen or Type IV collagen), proteoglycan, fibronectin, and laminin or combinations thereof. It can be desirable to combine various cell types on the inner or outer surface of the fibers. For example, it can be desirable to include endothelial cells and pericyte, vascular smooth muscle cells or mesangial cells or fibroblasts or combinations thereof. It can also be useful to provide a feeder layer of cells, e.g., irradiated fibroblasts or other cells that can provide soluble factors and structural support to cells they are indirectly or directly in contact with.

The above-described filtration system and the above-described tubule processing system can be combined to create an artificial kidney. Such systems are described in U.S. Pat. No. 6,150,164, hereby incorporated by reference. A number of suitable materials for forming the hollow fiber are described in U.S. Pat. No. 6,150,164, hereby incorporated by reference.

A number of embodiments of the invention have been described. Nevertheless, it will be understood that various modifications may be made without departing from the spirit and scope of the invention. Accordingly, other embodiments are within the scope of the following claims.

What is claimed is:

1. A composition comprising isolated renal cells that express Flk-1 wherein fewer than 25% of the Flk-1 expressing cells also express Sca-1.

2. A method for isolating renal stem cells, comprising:
   obtaining isolated kidney cells; and
   purifying from the isolated kidney cells a population of cells that express Flk-1, wherein fewer than 25% of the Flk-1 expressing cells also express Sca-1.

3. The composition of claim 1 wherein the isolated renal cells contain a transgene.

4. The composition of claim 3 wherein the transgene encodes a therapeutically useful polypeptide.

5. The method of claim 2 wherein the purifying step comprises contacting the isolated kidney cells with an antibody that binds to Flk-1.

6. The composition of claim 1, wherein fewer than 10% of the Flk-1 expressing cells also express Sca-1.

7. The composition of claim 8, wherein fewer than 5% of the Flk-1 expressing cells also express Sca-1.

8. The composition of claim 9, wherein fewer than 1% of the Flk-1 expressing cells also express Sca-1.

9. The composition of claim 8, wherein fewer than 0.1% of the Flk-1 expressing cells also express Sca-1.

10. The method of claim 2, wherein fewer than 10% of the Flk-1 expressing cells also express Sca-1.

11. The method of claim 10, wherein fewer than 5% of the Flk-1 expressing cells also express Sca-1.

12. The method of claim 11, wherein fewer than 1% of the Flk-1 expressing cells also express Sca-1.

13. The method of claim 12, wherein fewer than 0.1% of the Flk-1 expressing cells also express Sca-1.

14. The cells isolated according to the method of claim 2.

* * * * *

UNITED STATES PATENT AND TRADEMARK OFFICE
CERTIFICATE OF CORRECTION

PATENT NO. : 6,458,588 B1 Page 1 of 1
APPLICATION NO. : 09/826698
DATED : October 1, 2002
INVENTOR(S) : Peter G. Linde and M. Amin Arnaout It is certified that error appears in the above-identified patent and that said Letters Patent is hereby corrected as shown below:

On column 1, before TECHNICAL FIELD, please insert the following paragraph:

--REFERENCE TO GOVERNMENT RIGHTS

This invention was made with Government support under Grant Number DK54711 awarded by the National Institute of Health. The Government has certain rights to this invention.--

Signed and Sealed this

Seventh Day of November, 2006

JON W. DUDAS
*Director of the United States Patent and Trademark Office*